(12) United States Patent
Buchanan

(10) Patent No.: US 6,936,067 B2
(45) Date of Patent: Aug. 30, 2005

(54) PROSTHETIC HEART VALVE WITH SLIT STENT

(75) Inventor: Eric S. Buchanan, Wyoming, MN (US)

(73) Assignee: St. Jude Medical Inc., St. Paul, MN (US)

( * ) Notice: Subject to any disclaimer, the term of this patent is extended or adjusted under 35 U.S.C. 154(b) by 0 days.

(21) Appl. No.: 09/860,092

(22) Filed: May 17, 2001

(65) Prior Publication Data

US 2002/0173842 A1 Nov. 21, 2002

(51) Int. Cl.⁷ .................................................. A61F 2/06
(52) U.S. Cl. ...................... 623/2.28; 623/2.14; 623/2.4
(58) Field of Search ................................ 623/2.1, 2.11, 623/2.12, 2.13, 2.14, 2.15, 2.17, 2.18, 2.19, 2.23, 2.28, 2.33, 1.24, 1.26, 900

(56) References Cited

U.S. PATENT DOCUMENTS

| | | | |
|---|---|---|---|
| 3,714,671 A | * | 2/1973 | Edwards et al. ............ 623/2.19 |
| 4,441,216 A | | 4/1984 | Ionescu et al. ................. 3/1.5 |
| 4,470,157 A | | 9/1984 | Love ............................... 3/1.5 |
| 4,501,030 A | | 2/1985 | Lane ............................... 3/1.5 |
| 4,605,407 A | * | 8/1986 | Black et al. ................ 623/2.17 |
| 4,687,483 A | | 8/1987 | Fisher et al. .................... 623/2 |
| 4,725,274 A | | 2/1988 | Lane et al. ...................... 623/2 |
| 5,163,955 A | | 11/1992 | Love et al. ...................... 623/2 |
| 5,423,887 A | | 6/1995 | Love et al. ...................... 623/2 |
| 5,489,298 A | | 2/1996 | Love et al. ...................... 623/2 |
| 5,562,729 A | | 10/1996 | Purdy et al. .................... 623/2 |
| 5,728,152 A | | 3/1998 | Mirsch, II et al. ............. 623/2 |
| 5,910,170 A | | 6/1999 | Reimink et al. ................ 623/2 |
| 5,928,281 A | * | 7/1999 | Huynh et al. ............... 623/2.14 |

FOREIGN PATENT DOCUMENTS

EP      0 179 562 B1      9/1985

OTHER PUBLICATIONS

"Edwards Prima™ Stentless Bioprosthesis Modified Model 2500" by Baxter Edwards, AG, Switzerland (1996).

* cited by examiner

Primary Examiner—Corrine McDermott
Assistant Examiner—William H Matthews
(74) Attorney, Agent, or Firm—Westman, Champlin & Kelly, P.A.

(57) ABSTRACT

A valve prosthesis includes a plurality of flexible leaflets and a stent having a central lumen. A slit in the stent extends from the central lumen to an outer surface. An occluding portion of the flexible leaflets extends across the central lumen and an attachment portion extends from the central lumen through the slit and forms a sewing cuff for attachment to a patient's tissue. The attachment portion forms a sewing cuff for attachment to native heart tissue.

39 Claims, 9 Drawing Sheets

PROSTHETIC HEART VALVE WITH SLIT STENT

FIELD OF THE INVENTION

The present invention relates to prosthetic heart valves. More specifically, the present invention relates to attachment of a biocompatible material of a prosthetic heart valve to a native tissue annulus.

BACKGROUND OF THE INVENTION

Prosthetic heart valves have been used for replacing damaged or diseased heart valves in patients. Various types of prosthetic heart valves are known, including mechanical heart valves and bioprosthetic heart valves. Bioprosthetic heart valves may include a material, such as tissue or synthetic polymers, carried on a stent. The material typically comprises animal tissue, such as porcine aortic valve material or bovine pericardium.

Different techniques are known for coupling the material to the stent. For example, suturing the valve material to the stent is one common technique. However, such suturing has been found to place stress on the material as the valve opens and closes, thus leading to a shorter useful life for the prosthetic heart valve. In fact, any attachment technique which creates a hole in the tissue near the post tips may concentrate destructive stresses in those areas.

Various types of attachment techniques are shown in, for example, U.S. Pat. No. 4,501,030, issued Feb. 26, 1985, entitled "METHOD OF LEAFLET ATTACHMENT FOR PROSTHETIC HEART VALVES", U.S. Pat. No. 4,441,216 issued Apr. 10, 1984, entitled "TISSUE HEART VALVE AND STENT", U.S. Pat. Nos. 5,163,955, 5,423,887 and 5,489,298 to Love and U.S. Pat. No. 4,725,274, to Lane which issued Feb. 16, 1988.

One limitation frequently found in prior art stented valves is that the mechanism which attaches the leaflet to the stent prevents the leaflet from fully opening. This reduces the maximum diameter of the central lumen through the valve and impedes blood flow. Further, the leaflets can experience high stress in the attachment region. Stentless heart valves are also known in the art. However, such valves typically require more then one suture line to implant. Further, because they are not rigid, they may be more difficult to position correctly than stented valves.

SUMMARY OF THE INVENTION

In one aspect, a valve prosthesis is provided which includes a plurality of flexible leaflets and a stent. The stent has a central lumen, an outer surface and a slit extending from the central lumen to the outer surface. An occluding portion of the flexible leaflets extends across the central lumen. The flexible leaflets include an attachment portion which extends from the central lumen through the slit proximate to the outer surface.

In another aspect, a method for assembling a valved prosthesis which includes a plurality of flexible leaflets and a stent having a central lumen is provided. The stent has an outer surface and a slit extending from the central lumen to the outer surface. The leaflets extend through the slit. The method includes securing an attachment portion of the leaflets to a native tissue annulus.

DETAILED DESCRIPTION OF THE PREFERRED EMBODIMENTS

Figure 1:
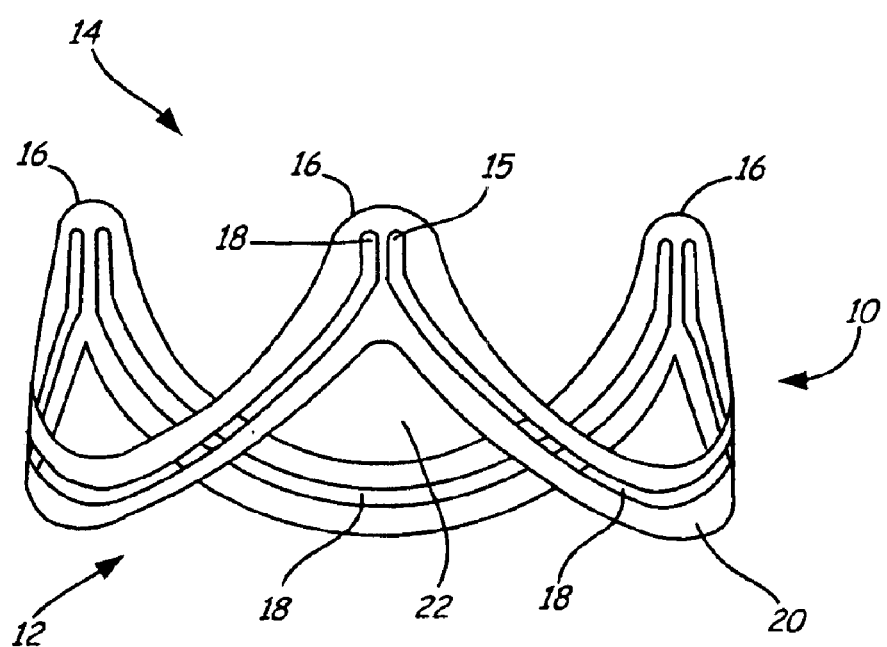
FIG. 1 is a side plan view of a stent for a valve prosthesis in accordance with the present invention.

FIG. 1 is a side plan view of a stent 10 in accordance with the present invention. Stent 10 includes an inflow opening 12, an outflow opening 14 and commissure posts 16 with scallops extending between posts. The shape of stent 10 generally matches the native valve geometry such that the leaflets will coapt properly. As shown in FIG. 1, stent 10 includes slits 18 which extend between posts 16 and from an outer surface 20 to a central lumen 22 through the stent 10. The vertical portion 15 of slits 18 ensure proper coaptation of adjacent leaflets. In general, it is preferable to have vertical slits 15 as close as possible to one another such that there are no gaps between adjacent leaflets, thereby reducing leakage between adjacent leaflets. Slits 18 should be wide enough to just allow the leaflets 42 to pass through. The slits can extend over any length of the stent. In one specific example, they extend about 95%, or more, of the distance to the tip of the commissure. Preferably, stent 10 is formed of a biocompatible material, such as polyetheretherketone (PEEK), or polyacetals (i.e., Delrin®). The slits can be formed in an injection mold or machined into the stent.

Figure 2A:
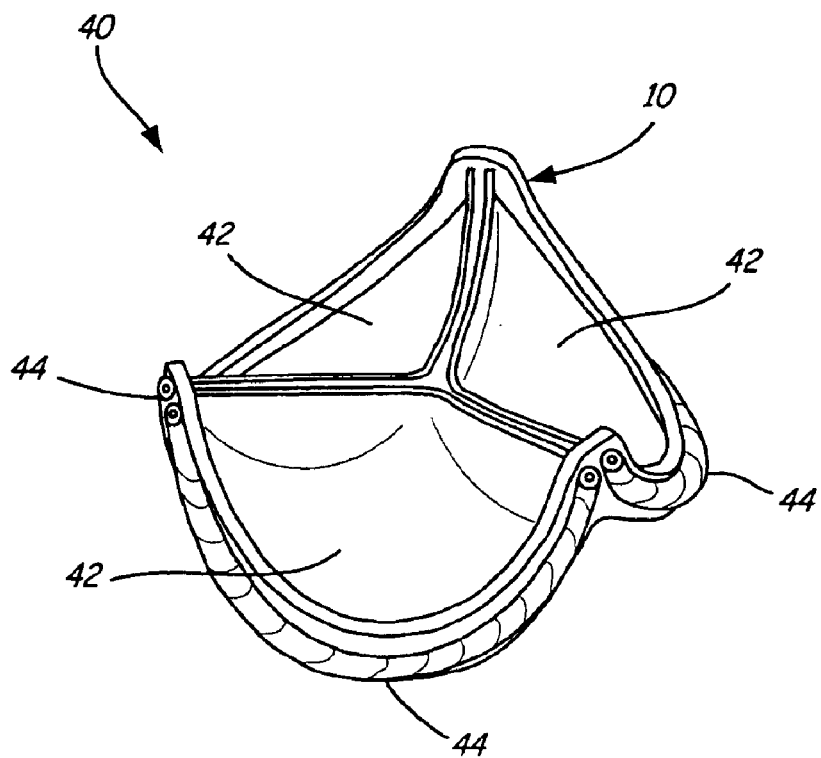
FIGS. 2A and 2B are perspective views of a valve prosthesis having the stent of FIG. 1.
Figure 2B:
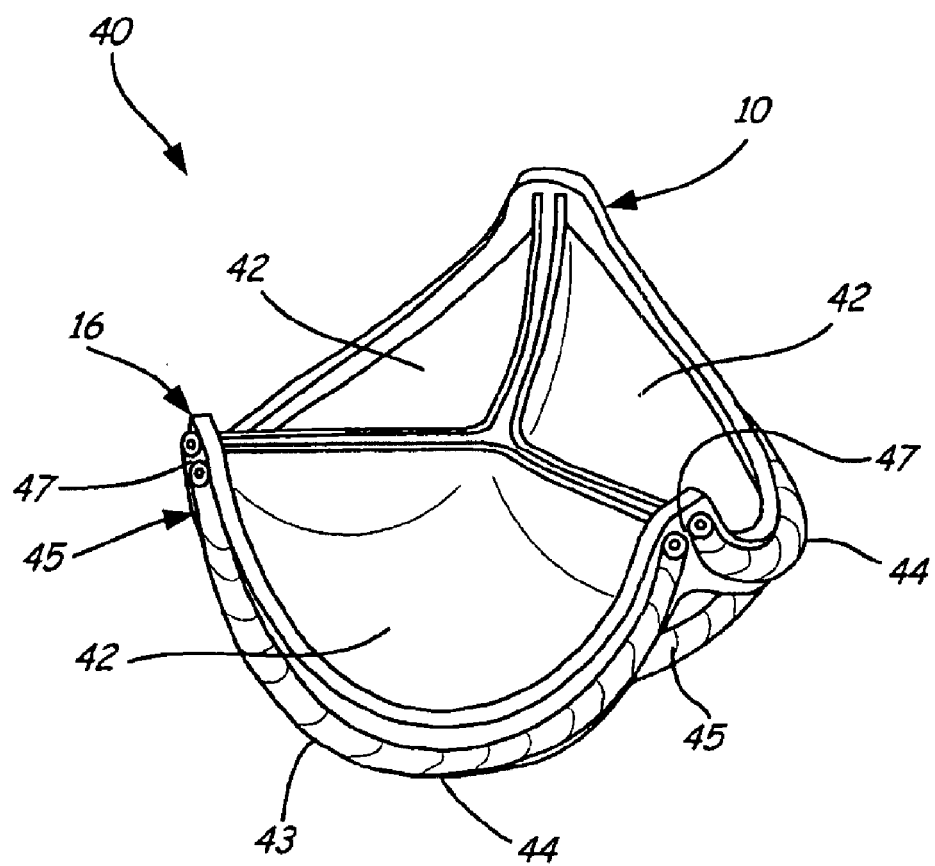
Figure 3:
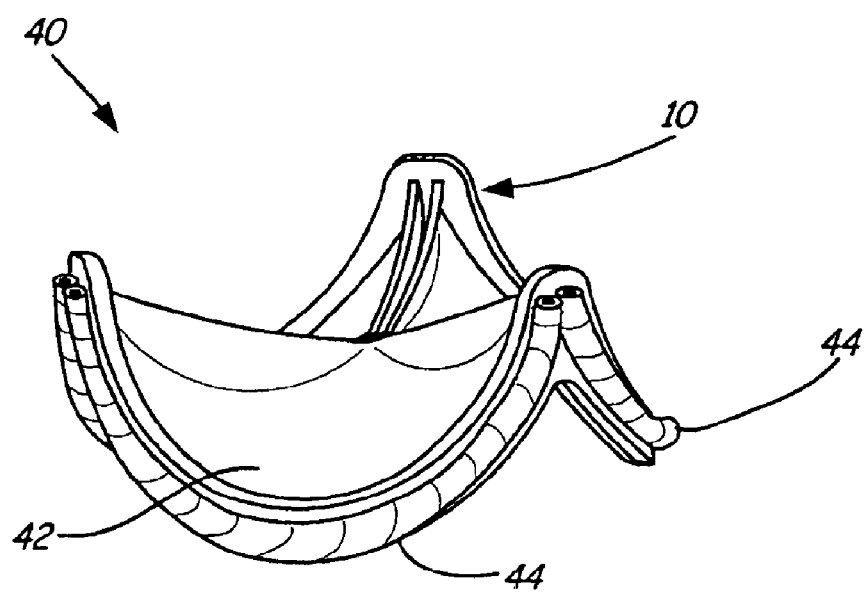
FIG. 3 is a side plan view of the valve prosthesis of FIG. 2A.

FIG. 2A is a perspective view of a valve prosthesis 40 including stent 10 shown in FIG. 1, and FIG. 3 is a side plan view. Valve prosthesis 40 includes three leaflets 42 supported in stent 10. The leaflets 42 extend from the central lumen 22 through slits 18 to the outer surface 20 shown in FIG. 1 to form attachment portions 44. Attachment portions 44 can be used as a sewing or suture cuff for attachment of the prosthesis 40 to the native tissue annulus in a patient. Although FIGS. 2A and 2B show three leaflets 42, the stent 10 can be modified as will be apparent to those skilled in the art, to accommodate other leaflet configurations and numbers, such as two leaflets, or four leaflets. In FIG. 2A, the leaflets 42 are shown in a closed position which blocks blood flow in a direction from the outflow opening toward the inflow opening. If the flow is in the opposite direction, the leaflets will open and allow blood flow through the central lumen 22 of the prosthesis 40.

Attachment portions 44 from adjacent leaflets can be coupled together at the commissure posts 16 where the adjacent attachment portions 44 meet on the outer surface 20. The coupling preferably provides a seal to prevent blood flow therethrough and can be made by means of sutures, biocompatible pieces of tissue or fabric which cover the joint, adhesives or other coupling techniques.

FIG. 2B is a perspective view of another embodiment. In FIG. 2B, a suture cuff extends adjacent the commissure posts 16. This allows the valve 40 to be more easily sutured to the tissue annulus. For example, the surgeon can suture the inflow edge with the attachment portions 44 along most of the scallop 43, then along the suture cuff 45 and onto the next scallop 43. After the inflow edge is sutured, the valve 40 is "parachuted" into position and cuff/attachment portions 47 are sutured to the aorta. With this configuration, the inflow edge, which is sutured, is generally in a single plane which makes attachment and parachuting easier.

Figure 4:
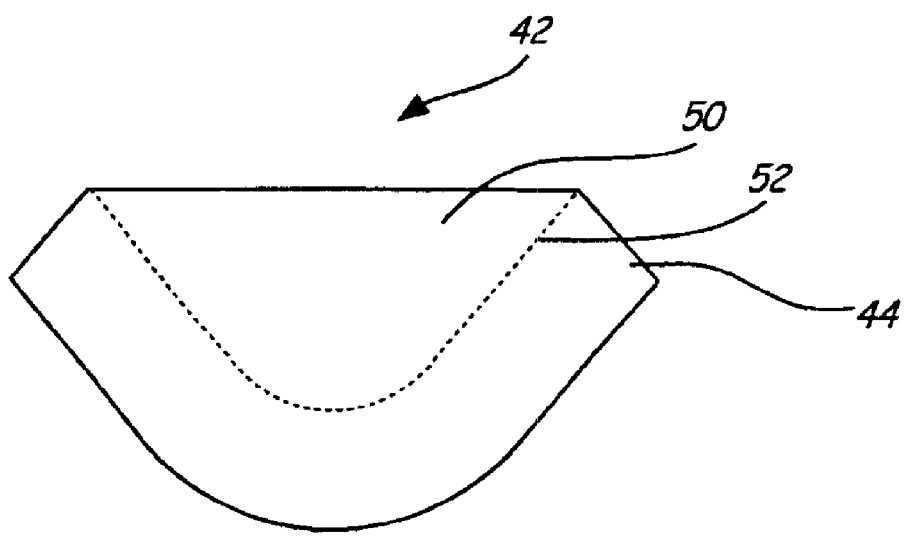
FIG. 4 is a plan view of a leaflet for use in the valve prosthesis of FIGS. 2A and 3.

FIG. 4 is a plan view of a leaflet 42. Leaflet 42 includes attachment portion 44 and valve portion 50. When assembled, attachment portion 44 is on the outer surface 20 of stent 10 and attaches to the patient's annulus. The valve portion 50 is positioned in the central lumen 22 and forms one of the leaflets of the valve. The slit 18 of stent 10 generally follows the profile shown by dashed line 52.

Figure 5:
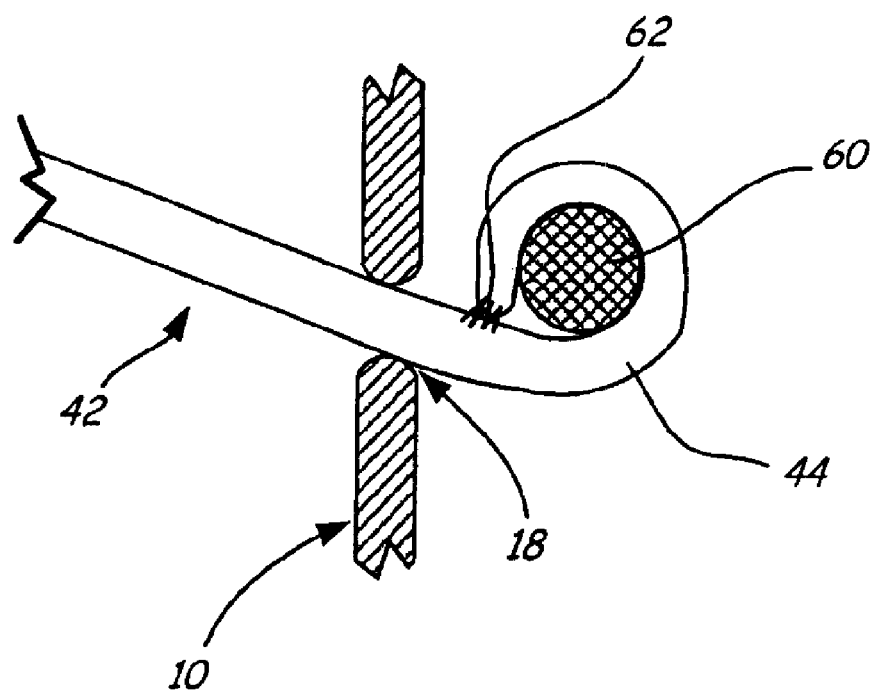
FIG. 5 is a side cross-sectional view showing one embodiment of an attachment portion of the valve prosthesis of FIGS. 2A and 3.
Figure 6:
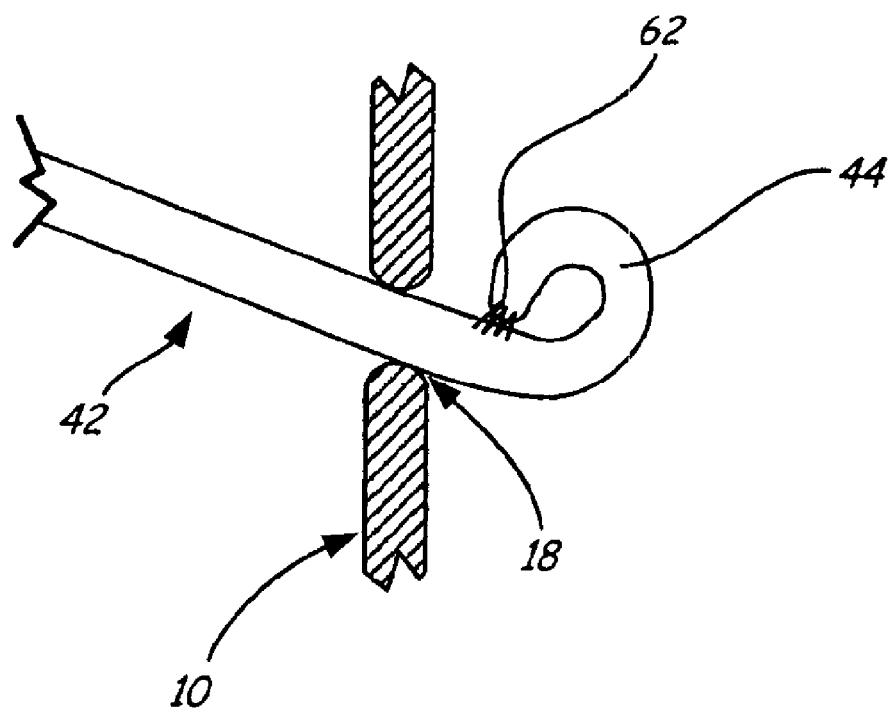
FIG. 6 is a cross-sectional view of another embodiment of an attachment portion of the valve prosthesis of FIGS. 2A and 3.

The attachment portion 44 can be formed using any appropriate technique. FIGS. 5 and 6 are cross-sectional views through a portion of stent 10 showing attachment portions 44. In FIG. 5, attachment portion 44 is formed by rolling leaflet 42 around a core 60. Core 60 can be any appropriate biocompatible material such as silicone, fabric including felt or fabric, such as polyester or PTFE, etc. The core 60 is preferably of a material which can receive a suture therethrough. The leaflet is then attached to itself, for example, using a suture 62, an adhesive, staples, or other attachment mechanism. FIG. 6 shows a core-less embodiment in which the leaflet 42 is wound on itself and attached to itself by suture 62, adhesive, staples or similar attachment mechanism. The width of the rolled attachment portion 44 is greater than the width of slit 18 to prevent the leaflet 42 from being removed from the stent 10. Although sutures are shown, any attachment technique can be used, including adhesives. In some embodiments, the leaflet is not rolled.

Figure 7:
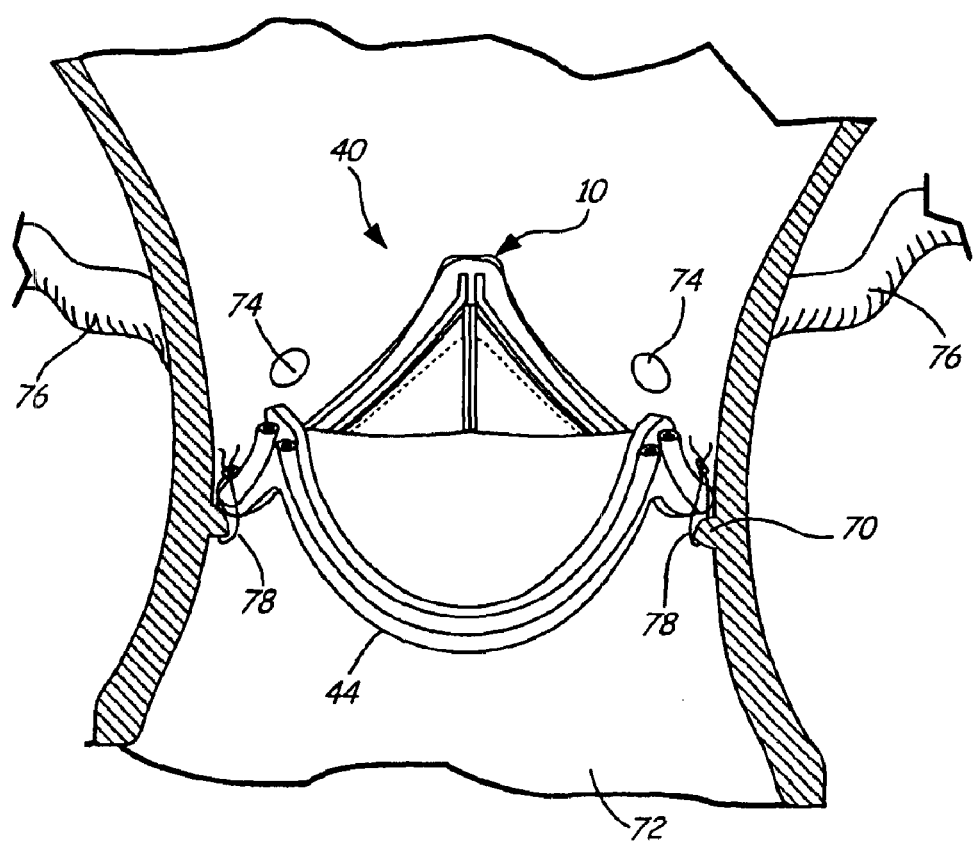
FIG. 7 is a cutaway view of the valve prosthesis of FIGS. 2A and 3 coupled to a tissue annulus of a heart.
Figure 8:
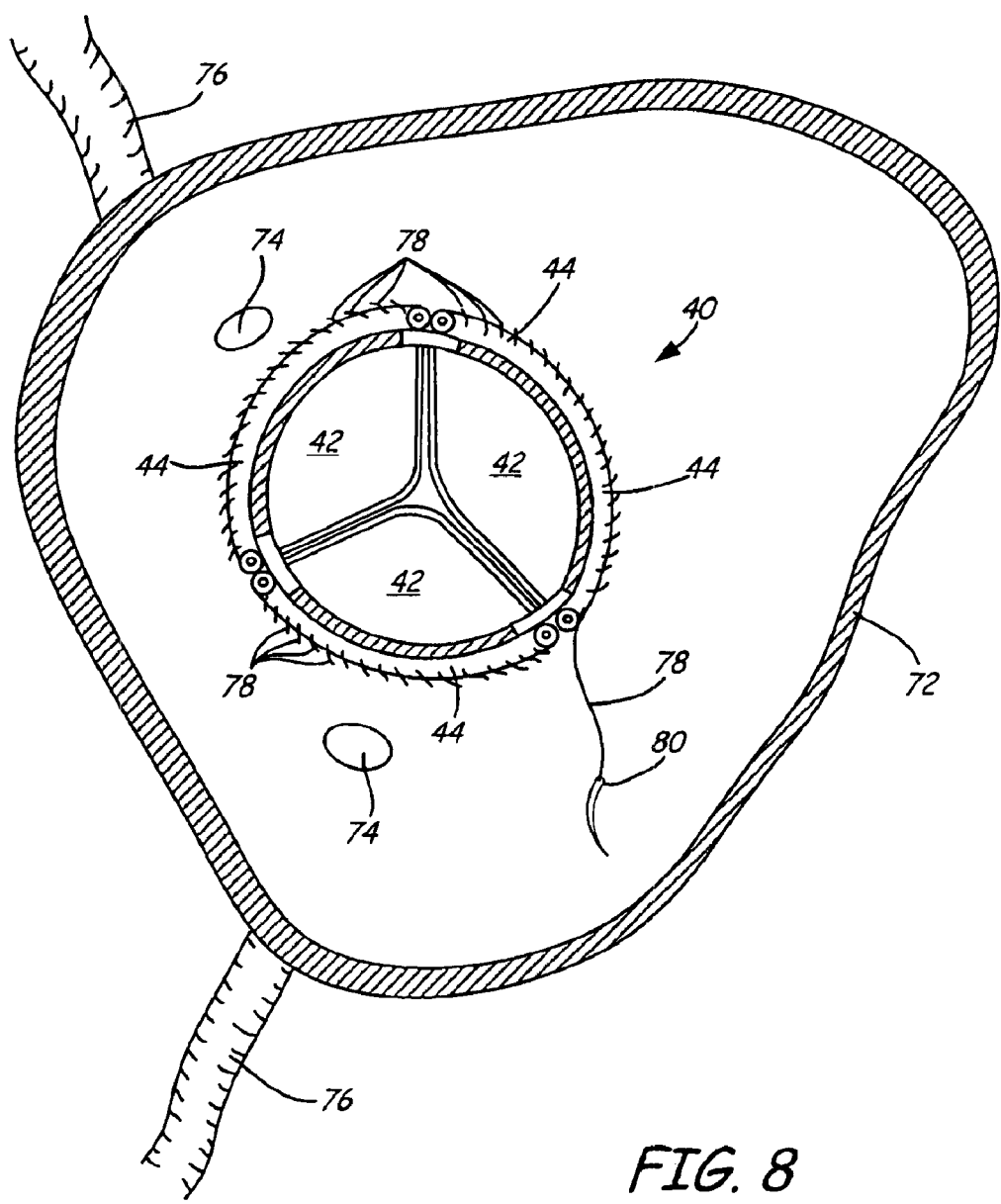
FIG. 8 is a top plan view of the valve prosthesis in the heart illustrated in FIG. 7.

FIG. 7 is a side cutaway view and FIG. 8 is a top plan view of valve prosthesis 40 positioned in a native tissue annulus 70 of a heart. In these illustrations, valve prosthesis 40 is configured to allow blood flow out of aorta 72 and block blood flow in the opposite direction. FIGS. 7 and 8 also illustrate the position of the valve prosthesis 40 relative to coronary ostia 74 which couple to coronary arteries 76.

As illustrated in FIG. 7, sutures 78 are used to attach the attachment portions 44 to the annulus 70. FIG. 8 shows the valve 40 substantially completely sutured to the tissue annulus 70. In FIG. 8, needle 80 can be used to complete the suturing process. The attachment portion 44 of leaflets 42 are sutured directly to the aortic wall. After suturing, the leaflets are supported by the aortic wall and not by the stent. With the present invention, the leaflets are attached to the aortic wall to maximize the valve opening and minimize the stress concentrations in the leaflets like with a stentless valve. With the invention, the stent 10 allows for easier implantation with a single suture line.

In operation, to form valve prosthesis 40, leaflets 42 are cut using a template from a tissue or flexible polymer material. The attachment portion 44 of leaflet 42 is slid through slit 18 so that a sufficient amount of leaflet 42 to form the attachment portion extends from outer surface 20. Attachment portion 44 is then formed by winding or rolling leaflet 42 on itself, or by rolling leaflet 42 around a core material 60. Adjacent leaflet attachment portions 44 are coupled on the outer surface 20 at the commissure posts 16 of stent 10 by suture, adhesives, tissue or polymer material, and the like. Valve portion 50 of leaflet 42 is positioned within stent 10, forming leaflets of valve prosthesis 40. After the native leaflets have been excised, valve prosthesis 40 is implanted by suturing attachment portions 44 of prosthesis 40 into annulus 70.

A prosthetic valve in accordance with the present invention may be made with other types of stents than that shown specifically herein. For example, the stent may be formed of various materials and have a desired flexibility for a particular application. The slits can be arranged and configured as described with differing orientation and/or widths. The posts, or commissure supports, may be formed as desired having other characteristic configurations. The locations and the number of the posts may also be varied. The stent generally is configured to support leaflets that mimic the function of natural valves, which close to prevent backflow through the valve and open to provide little if any resistance to forward flow. The stent may be coated with polytetrafluoroethylene (PTFE) or may include a fabric, tissue, or other covering or wrap to reduce wear on the leaflets. Preferably, the stent is semi-rigid or rigid.

The stent and core may be produced of any appropriate biocompatible material, e.g., material compatible with blood and/or tissue. Practical considerations suggest the use of commercially available medical materials. For example, these parts may be formed or preformed from any metal, synthetic polymer, biopolymer, composite materials, etc. which is capable of supporting the leaflets during implantation. It may also be desirable to sterilize the material by exposure to gas plasma, steam, gamma or electron beam irradiation, or chemical sterilization such as ethylene oxide, formaldehyde, glutaraldehyde, peroxides, and propylene oxide, and preferably any such material is capable of withstanding such exposure. The invention is not limited to any particular material used to construct the stent, leaflets, or core, etc., and includes other materials, combinations, etc.

Preferred materials for stents are synthetic, polymeric materials, and most preferred are materials that can be injection molded. Materials such as Eligiloy®, as well as various polymers, biopolymers, PEEK, and polyacetals such as Delrin® can be used.

For any of the embodiments, if the support stent is formed from a rigid or semi-rigid material that supports the leaflets, suitable materials include, for example, rigid or semi-rigid polymers, metals, ceramics, carbon materials and combinations thereof. Suitable polymers include, for example, polyacetals, such as Delrin® and Celcon®, polysulfones, polyethersulfones, polyarylsulfones, polyetherimides, and polyetheretherketones. Other synthetic polymers that may be useful include polyamides (nylon), polyesters, polystyrene, polyacrylates, vinyl polymers (e.g., polyethylene, polytetrafluoroethylene (PTFE), polypropylene and polyvinylchoride), polycarbonate, polyurethane, polydimethyl siloxane, cellulose acetate, polymethyl methacrylate, ethylene vinyl acetate, and similar copolymers. Biological polymers that may be used include natural forms such as collagen, elastin and cellulose, synthetic biopolymers, such as polyaminoacids or synthetic proteins, or purified biopolymers such as polyaminoacids or polysaccharides. Polymers generally can be molded or cast into the selected forms or can be knit or woven into a mesh to form a matrix.

Suitable metals include biocompatible metals, such as stainless steel, titanium, cobalt alloys, such as Elgiloy®, a cobalt-chromium-nickel alloy, and MP35N, a nickel-cobalt-chromium-molybdenum alloy, and Nitinol, a nickel-titanium alloy. Heart valve stents made from spring metals, such as Elgiloy®, exhibit good mechanical properties, such as strength and fatigue endurance, and can have a smaller cross-section than corresponding polymer stents. Composite metal/polymer heart valve stents are described in copending and commonly assigned U.S. patent application Ser. No. 09/475,721 to Reimink et al., entitled "MEDICAL DEVICES WITH POLYMER/INORGANIC SUBSTRATE COMPOSITES," incorporated herein by reference. In addition, stents can be produced from ceramic materials, such as pyrolytic carbon, silicon carbides/nitrides or metal carbides/nitrides, cermets, hydroxyapatite, zirconia and alumina. Suitable stents can also be produced from carbons, such as graphite.

Suitable polymers for support structures also include resorbable polymers, such as dextran, hydroxyethyl starch, gelatin, derivatives of gelatin, polyvinylpyrrolidone, polyvinyl alcohol, poly[N-(2-hydroxylpropyl)methacrylamide], polyesters, polyglycols, poly(orthoesters), poly(ester amides), and polyanhydrides. Resorbable polyesters include, for example, poly(hydroxy acids) and copolymers thereof, poly($\epsilon$-caprolactone), poly(dimethyl glycolic acid), and poly(hydroxy butyrate). Preferred resorbable polymers include, for example, D, L-polylactic acid, L-polylactic acid, poly(glycolic acid), and copolymers of L-lactic acid, D-lactic acid and glycolic acid. The formation of heart valve stents from resorbable polymers is described further in U.S. Pat. No. 5,728,152 to Mirsch II et al., entitled "Bioresorbable Heart Valve Support," incorporated herein by reference.

The core can be of any appropriate biocompatible material such as, felt, polyester, PTFE, silicone, flexible biocompatible polymer or material through which a needle can pass.

The leaflets can be formed from tissue or flexible polymers. Biological materials for use in this invention include relatively intact tissue as well as decellularized or otherwise modified tissue. Appropriate tissues also include tissue equivalents such as tissue-engineered material involving a cell-repopulated matrix, which can be formed from a polymer or from a decellularized natural tissue.

Natural, i.e. biological, tissue material for use in the invention includes relatively intact tissue as well as decellularized tissue. These natural tissues may be obtained from, for example, native heart valves, portions of native heart valves such as roots, walls and leaflets, pericardial tissues such as pericardial patches, amniotic sacs, connective tissues, bypass grafts, tendons, ligaments, skin patches, blood vessels, cartilage, dura mater, skin, bone, fascia, submucosa, umbilical tissues, and the like.

Natural tissues are derived from a particular animal species, typically mammalian, such as human, bovine, porcine, seal or kangaroo, as well as engineered tissues. These tissues may include a whole organ, a portion of an organ or structural tissue components. Suitable tissues include xenografts, homografts and autografts. These natural tissues generally include collagen-containing material. Tissue materials are particularly useful for the formation of tissue heart valve prostheses. The tissue can be decellularized. Engineered tissue typically involves repopulated matrices which can be derived from the tissues mentioned above or synthetically fabricated.

Tissues can be fixed by crosslinking. Fixation provides mechanical stabilization, for example, by preventing enzymatic degradation of the tissue, although the tissues do not necessarily need to be fixed. Glutaraldehyde, formaldehyde or a combination thereof is typically used for fixation, but other fixatives can be used, such as epoxides, diimides, photooxidation and other difunctional aldehydes. In particular, aldehyde functional groups are highly reactive with amine groups in proteins, such as collagen.

Besides crosslinking, the tissue can be treated with other compounds to modify the tissue properties. In preferred embodiments, the tissue is treated with calcification reducing compounds. For glutaraldehyde crosslinked tissue, preferred anticalcificaton agents include, for example, multivalent metal cations, such as $Al^{+3}$. The tissues can be treated with other agents to impart desirable properties, such as growth factors and the like.

Suitable polymeric materials for formation into the leaflets include, for example, synthetic polymers as well as purified biological polymers and combinations thereof. Flexible polymers include elastomers and other polymers that can sustain significant flexure, bending, twisting, wear and/or deformation without structural failure. Appropriate synthetic polymers include, without limitation, polyamides (e.g., nylon), polyesters, polyacrylates, vinyl polymers (e.g., polyolefins, polyethylene, polytetrafluoroethylene or other halogenated polymers, polypropylene, ethylene-propylene copolymers, ethylene-propylene-diene monomer copolymer (EPDM) and polyvinylchloride), polycarbonates, polyacetals (e.g., Delrin®), polyurethanes, polydimethyl siloxanes, cellulose acetates, ethylene vinyl acetates, polysulfones, nitrocelluloses, derivatives thereof, similar copolymers, and mixtures thereof. Particularly preferred flexible polymer materials for the formation of flexible polymer heart valve leaflets include, for example, polyurethanes, polydimethyl siloxanes, polytetrafluoroethylene, derivatives thereof and mixtures thereof. Polymer leaflets can be formed by casting, molding and the like. Preferred methods include dip coating with a mandrel.

Materials which comprise either the stent, core or leaflets can remain untreated or can be treated to effect a desired result, for example, to make the part(s) more effective within the environment of the heart. The modification can be in the form of surface finish alterations or in chemical modifications applied to the stent, core or leaflet material. Surface finish alterations include smoothing or softening the stent or leaflet in the region of the slit to reduce wear. Surface texture can also be added to the external surfaces of the stent to optimize cell adhesion and growth. To achieve this end, the surface finish of some portions of the stent may require a reduction in roughness. Ideally, the surface finish of different surface locations on the stent may be tuned independently to optimize the characteristics of the entire prosthesis. For example, a substrate can be associated with one or more growth factors, such as vascular endothelial growth factor (VEGF) and/or fibroblast growth factor, and/or attraction compounds that recruit cells, including precursor cells, to the tissue.

Appropriate chemical modifications to these materials can include any or all of the following. Thrombogenicity of the surface can be modified, for example with heparin. Other modifiers such as fibronectin or other arginine-glycine-aspartic acid (RGD) sequence containing peptides can be used to modify the healing response of the part(s). Additionally, growth factors such as fibroblast or endothelial cell growth factors or other chemotactants can be applied to improve biocompatability.

The present invention reduces the stress applied to the leaflets in the region where they are normally attached to the stents. Instead, the leaflets are supported directly by the native tissue. With the present invention, the stent is primarily used to support the leaflets prior to implantation. The stent also provides rigidity so that the valve can be positioned during implantation. Once the prosthesis is implanted, the leaflets are directly coupled to the tissue annulus and do not require substantial support from the stent. This configuration spreads the stress associated with operation of the valve over a larger area, thereby reducing localized stress on the leaflet. By attaching leaflets directly to aortic wall, the leaflets and aorta share the pressure load associated with the valve operation. By sharing the load, the stress is less in the leaflet. Implantation can be through a single suture line because the stent provides rigidity to maintain leaflet geometry until implantation is complete. In the preferred embodiment, the attachment portion is formed using a suture or an adhesive. An optional core can also be used.

In various aspects, the invention provides a simple and easy to manufacture design that allows a stentless valve to be implanted like a stented valve. Typical stentless valves include aortic root material which maintains the proper leaflet geometry and to which the leaflets are attached. This aortic root material reduces the size of the device that can be implanted and can be prone to calcification leading to eventual valve failure. With this invention, the aortic root material is unnecessary because the stent maintains the proper leaflet geometry and provides enough rigidity to allow the valve to be parachuted into place with a single line of interrupted sutures. Since the cuff is an integral part of the leaflet, after implantation, the leaflets are attached directly to the aortic wall. After attachment, the stent prevents radial intrusion of the aortic wall and maintains the leaflet free edges in a configuration that is conducive to coaptation. The stent is not directly loaded by the leaflet. The closed valve pressure load is transferred directly to the aortic wall via the implant sutures. The stent is only deflected indirectly if the aortic wall pushes it inwardly. In a native valve, the commissures expand during systole to open the valve beyond its diastolic dimensions. With this stent design, the leaflets can open more fully than a typical stented prosthetic valve. During systole, the aorta expands, and since the leaflets are attached to the aortic wall, and the leaflets can slide through the slit in the stent, the aortic wall causes the leaflets to open more fully.

Implanting the valve of the present invention along the scalloped inflow edge may be facilitated by the use of suture marking tools similar to those in patent application Ser. No. 09/561,544, filed Apr. 28, 2000, entitled "AORTIC HEART VALVE PROSTHESIS SIZER AND MARKER" which is hereby incorporated by reference in its entirety. These tools can be modified to represent the valve geometry of the present invention and can be used to mark the scalloped shape in the annulus such that the sutures in the annulus will match with the sutures placed in the suture or sewing cuff when the valve is parachuted into place. Additionally, in some embodiments, the stent is removed after implantation by sliding the stent over the leaflets or by cutting the stent, or the stent may be resorbed over if a bioresorbable polymer was used.

Although the present invention has been described with reference to preferred embodiments, workers skilled in the art will recognize that changes may be made in form and detail without departing from the spirit and scope of the invention.

What is claimed is:

1. A valve prosthesis comprising a plurality of flexible leaflets and a stent having a central lumen, an outer surface and a slit extending from the central lumen to the outer surface, an occluding portion of the flexible leaflets extending across the central lumen, wherein the flexible leaflets are supported by the stent and a portion of at least one of the flexible leaflets slidably extends through the slit from the central lumen to the outer surface, the at least one flexible leaflet having an attachment portion, the attachment portion having a rolled rim positioned entirely outside the outer surface of the stent.

2. The valve prosthesis of claim 1 wherein the plurality of flexible leaflets comprises three leaflets.

3. The valve prosthesis of claim 1 wherein the flexible leaflets comprise tissue.

4. The valve prosthesis of claim 1 wherein the flexible leaflets comprise crosslinked tissue.

5. The valve prosthesis of claim 1 wherein the flexible leaflets comprise a polymer.

6. The valve prosthesis of claim 1 wherein the stent comprises a polyacetal.

7. The valve prosthesis of claim 1 wherein the stent comprises a polymer.

8. The valve prosthesis of claim 1 wherein the stent comprises a metal or metal alloy.

9. The valve prosthesis of claim 1 wherein the stent has a plurality of commissure posts connected by scallops.

10. The valve prosthesis of claim 9 wherein the slit extends along one of the scallops at least about 95 percent of the distance between two adjacent commissure posts.

11. The valve prosthesis of claim 1 further comprising a sewing cuff around at least a portion of the circumference of the valve prosthesis.

12. The valve prosthesis of claim 1 wherein the attachment portion of the leaflet is folded on itself and secured to itself to thereby form a suture cuff.

13. The valve prosthesis of claim 1 wherein the attachment portion of the leaflet is wound around a core to thereby form a suture cuff.

14. The valve prosthesis of claim 13 wherein the core comprises a polymer.

15. The valve prosthesis of claim 13 wherein the core comprises fabric.

16. The valve prosthesis of claim 13 wherein the core comprises silicone.

17. The valve prosthesis of claim 1 wherein the attachment portion of the leaflet is configured to attach to a tissue annulus of the heart and distribute stress during valve operation to the aortic wall.

18. The valve prosthesis of claim 1 wherein the stent provides support to the leaflets during implantation.

19. A valve prosthesis comprising a plurality of flexible leaflets and a stent having a central lumen, an outer surface and a slit extending from the central lumen to the outer surface, at least one flexible leaflet slidably extending through the silt to position a rolled rim of an attachment portion of the flexible leaflet outside the outer surface of the stent and a valve portion of the leaflet in the central lumen.

20. A valve prosthesis comprising a plurality of flexible leaflets and a stent having a central lumen, an outer surface and a slit extending from the central lumen to the outer surface, an occluding portion of the flexible leaflets extending across the central lumen, wherein the flexible leaflets are supported by the stent and an attachment portion of at least one of the flexible leaflets extends from the central lumen through the slit proximate to the outer surface, wherein the attachment portion of the leaflet extending through the slit on the outer portion of the stent is folded on itself and secured to itself to thereby form a suture cuff.

21. A valve prosthesis comprising a plurality of flexible leaflets and a stent having a ventral lumen, an outer surface and a slit extending from the central lumen to the outer surface, an occluding portion of the flexible leaflets extending across the central lumen, wherein the flexible leaflets are supported by the stent and an attachment portion of at least one of the flexible leaflets extends from the central lumen through the slit proximate to the outer surface, wherein the attachment portion of the leaflet extending through the slit is wound around a core to thereby form a suture cuff.

22. The valve prosthesis of claim 21 wherein the core comprises a polymer.

23. The valve prosthesis of claim 21 wherein the core comprises fabric.

24. The valve prosthesis of claim 21 wherein the core comprises silicone.

25. A valve prosthesis comprising a plurality of flexible leaflets and a stent having a central lumen, an outer surface and a slit extending from the central lumen to the outer surface, an occluding portion of the flexible leaflets extending across the central lumen, wherein the flexible leaflets are supported by the stent and an attachment portion of at least one of the flexible leaflets slidably extends through the slit from the central lumen to the outer surface, wherein the attachment portion of the leaflet extending through the silt on the outer portion of the stent is folded on itself and secured to itself to thereby form a suture cuff.

26. A valve prosthesis comprising a plurality of flexible leaflets and a stent having a central lumen, an outer surface and a slit extending from the central lumen to the outer surface, an occluding portion of the flexible leaflets extending across the central lumen, wherein the flexible leaflets are supported by the stent and an attachment portion of at least one of the flexible leaflets slidably extends through the slit from the central lumen to the outer surface, wherein the attachment portion of the leaflet extending through the slit is wound around a core to thereby form a suture cuff.

27. The valve prosthesis of claim 26 wherein the core comprises a polymer.

28. The valve prosthesis of claim 26 wherein the core comprises fabric.

29. The valve prosthesis of claim 26 wherein the core comprises silicone.

30. The valve prosthesis of claim 26 wherein the flexible leaflets comprise a material selected from the group consisting of tissue, crosslinked tissue, and polymeric materials.

31. The valve prosthesis of claim 26 wherein the stent comprises a polymer, a polyacetal, a metal or a metal alloy.

32. A valve prosthesis comprising a plurality of flexible leaflets and a stent having a central lumen, an outer surface and a slit extending from the central lumen to the outer surface, an occluding portion of the flexible leaflets extending across the central lumen, wherein the flexible leaflets are supported by the stent and a portion of at least one of the flexible leaflets slidably extends through the slit from the central lumen to the outer surface, the at least one flexible leaflet having an attachment portion positioned outside the outer surface, wherein the attachment portion of the flexible leaflet is movable relative to the stent, and wherein the attachment portion of the leaflet extending through the slit on the outer portion of the stent is folded on itself and secured to itself to thereby form a suture cuff.

33. A valve prosthesis comprising a plurality of flexible leaflets and a stent having a central lumen, an outer surface and a slit extending from the central lumen to the outer surface, an occluding portion of the flexible leaflets extending across the central lumen, wherein the flexible leaflets are supported by the stent and a portion of at least one of the flexible leaflets slidably extends through the silt from the central lumen to the outer surface, the at least one flexible leaflet having an attachment portion positioned outside the outer surface, wherein the attachment portion of the flexible leaflet is movable relative to the stent, and wherein the attachment portion of the leaflet extending through the-silt is wound around a core to thereby form a suture cuff.

34. The valve prosthesis of claim 33 wherein the core comprises a polymer.

35. The valve prosthesis of claim 33 wherein the core comprises fabric.

36. The valve prosthesis of claim 33 wherein the core comprises silicone.

37. The valve prosthesis of claim 33 wherein the flexible leaflets comprise a material selected from the group consisting of tissue, crosslinked tissue, and polymeric materials.

38. The valve prosthesis of claim 33 wherein the stent comprises a polymer, a polyacetal, a metal or a metal alloy.

39. A valve prosthesis comprising:

a stent having a central lumen and an outer surface;

leaflet means slidably extending through the stent from the central lumen to the outer surface for blocking blood flow in one direction through the stent; and attachment means formed from the leaflet means for attaching the leaflet means to a native tissue annulus of a heart, wherein the attachment means comprises a rolled rim located entirely outside the outer surface of the stent.

* * * * *